US00PP20705P3

(12) United States Plant Patent
Higaki

(10) Patent No.: US PP20,705 P3
(45) Date of Patent: Feb. 2, 2010

(54) *HYDRANGEA* PLANT NAMED 'GLORY'

(50) Latin Name: *Hydrangea macrophylla*
Varietal Denomination: Glory

(75) Inventor: Harrison Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 12/082,145

(22) Filed: Apr. 8, 2008

(65) Prior Publication Data

US 2009/0255019 P1 Oct. 8, 2009

(51) Int. Cl.
*A01H 5/00* (2006.01)

(52) U.S. Cl. ..... Plt./250

(58) Field of Classification Search ..... Plt./250
See application file for complete search history.

(56) References Cited

U.S. PATENT DOCUMENTS

PP15,912 P3 * 8/2005 Higaki ..... Plt./250

* cited by examiner

*Primary Examiner*—Susan B McCormick Ewoldt
(74) *Attorney, Agent, or Firm*—James R. Cypher; Charles R. Cypher

(57) ABSTRACT

A new and distinct cultivar of *Hydrangea macrophylla* (Thunb.) named 'Glory' originated as a controlled cross. The cultivar 'Glory' has non-pigmented sepalous florets and is desirable for its compact and sturdy growth habit. 'Glory' has large showy inflorescences, having both sepalous and non-sepalous florets, dominated non-sepalous florets.

4 Drawing Sheets

Botanical classification: *Hydrangea macrophylla* (Thunb.) 'Glory'.

Variety denomination: 'Glory'.

BACKGROUND OF THE INVENTION

The present invention relates to a new and distinct variety of the *Hydrangea*.

The new cultivar originated as a seedling from a controlled cross between the unpatented varieties 'Snowball' and 'Libelle,' with 'Snowball' being the pollen parent and 'Libelle' being the seed parent.

The variety 'Glory' has non-pigmented sepals. The new variety was first noticed, because it combined the desirable growth characteristics of its parents while producing flowers with non-pigmented sepals. The new variety has a compact growth habit, it produces showy blooms of uniform dimension, it blooms early, and it branches easily when pinched. In addition, the sepals of the new variety are resistant to turning brown when the plant experiences moderate drought and wilting and the sepals of the new variety are resistant to turning brown as the blooms age, thus the blooms are long-lasting. The following table compares the new variety to some of its closest varieties.

TABLE 1

| | New Variety 'Glory' | 'White Robe' U.S. Plant Pat. No. 15,192 | 'Supreme White' (U.S. Plant Pat. application No. 12/322,241 | 'Snowball' unpatented variety |
|---|---|---|---|---|
| Relative Height | Compact | Tall | Medium | Compact |
| Infloresence Uniformity | Excellent | Acceptable | Good | Poor |

TABLE 1-continued

| | New Variety 'Glory' | 'White Robe' U.S. Plant Pat. No. 15,192 | 'Supreme White' (U.S. Plant Pat. application No. 12/322,241 | 'Snowball' unpatented variety |
|---|---|---|---|---|
| Relative resistance to browning of sepals when stressed by moderate drought | Excellent | Excellent | Acceptable | Very Poor |
| Relative flower longetivity | Excellent | Good | Acceptable | Poor |
| Crop time | Very early | Late | Standard | Early |
| Relative ease of branching when pinched | Excellent | Acceptable | Good | Excellent |

The new cultivar 'Glory' has been successfully asexually reproduced under controlled environmental conditions at a nursery in Half Moon Bay, Calif. under the direction of the inventor over a three year period with its distinguishing characteristics remaining stable.

Asexual reproduction was first accomplished when vegetative cuttings were taken from the initially selected plant. Examination of asexually reproduced, successive generations grown in at Half Moon Bay, Calif. show that the combination of characteristics as herein disclosed for 'Glory' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
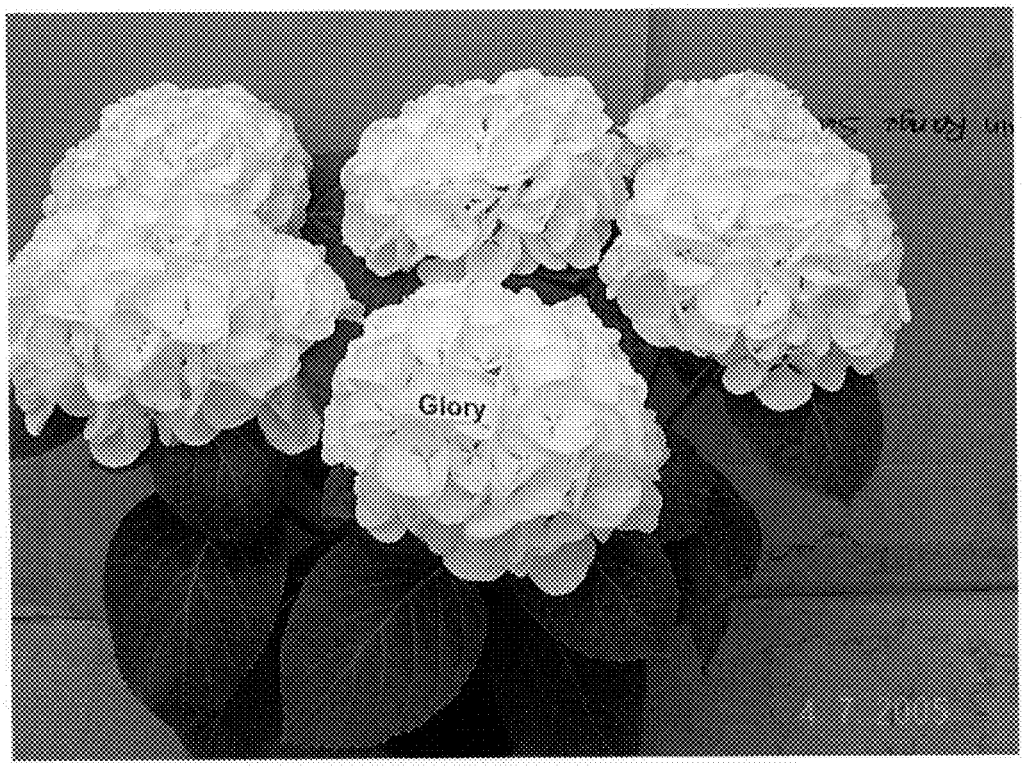
FIG. 1 is a view of the entire plant showing its form, compact growth habit, dark green foliage, inflorescence, and non-pigmented sepals.
Figure 2:
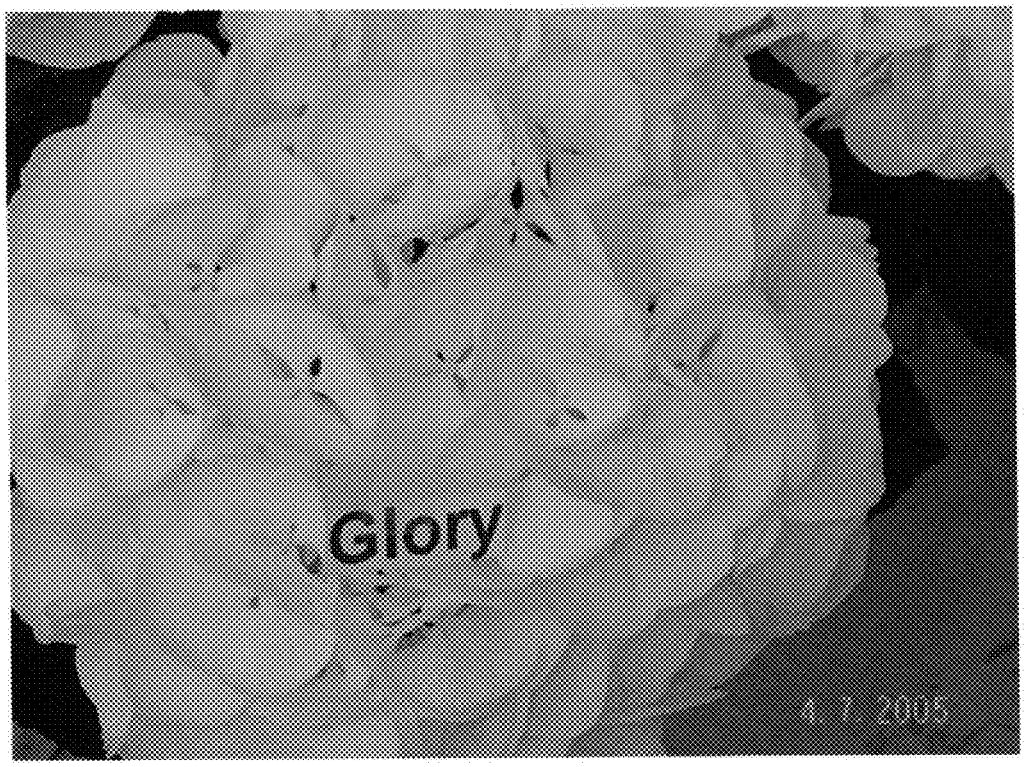
FIG. 2 is a close-up view of a panicle of the new variety, showing opened, sepalous florets.
Figure 3:
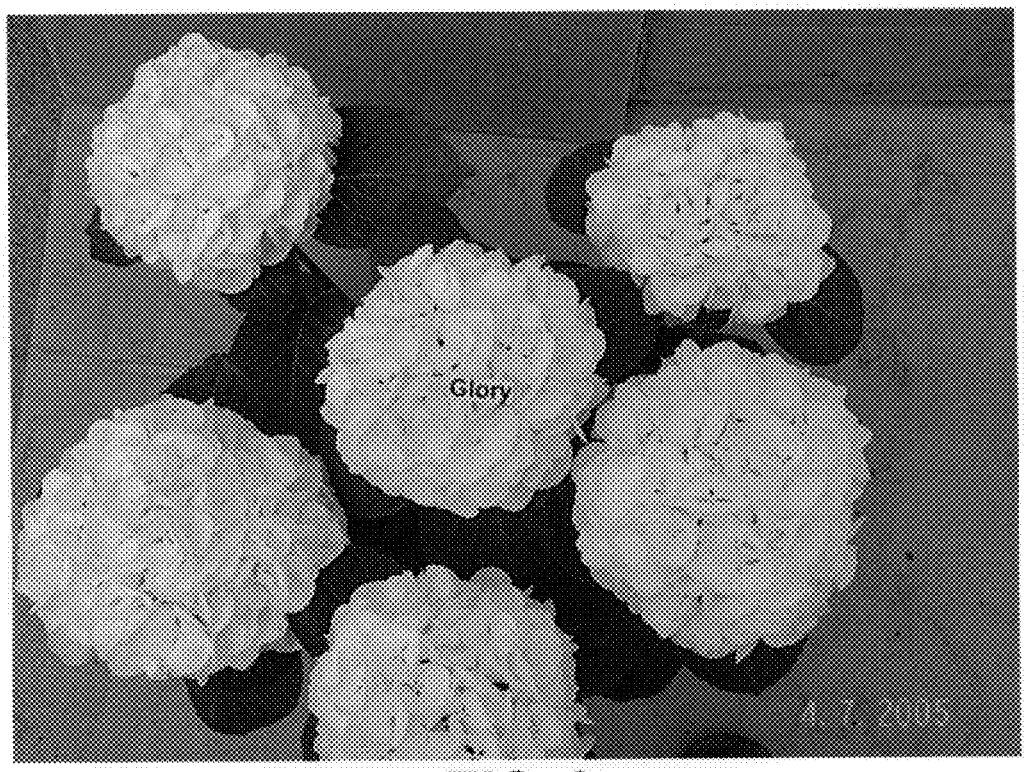
FIG. 3 is a top view of the new variety.
Figure 4:
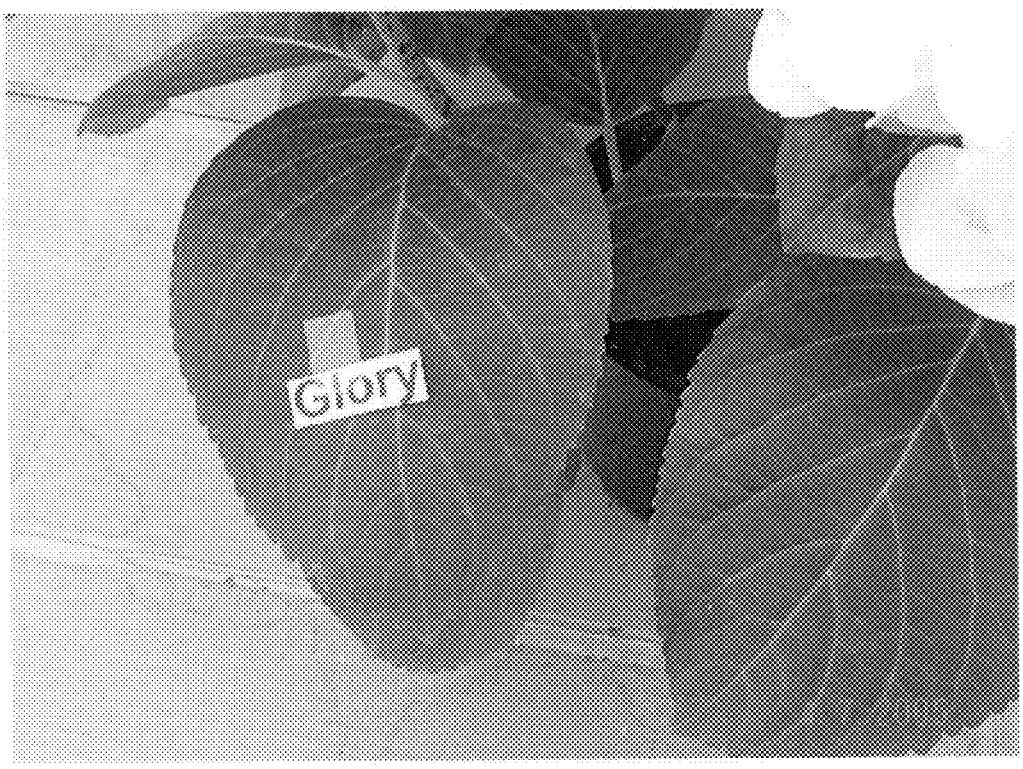
FIG. 4 is a close-up view of the adaxial surface of a mature leaf.
Figure 5:
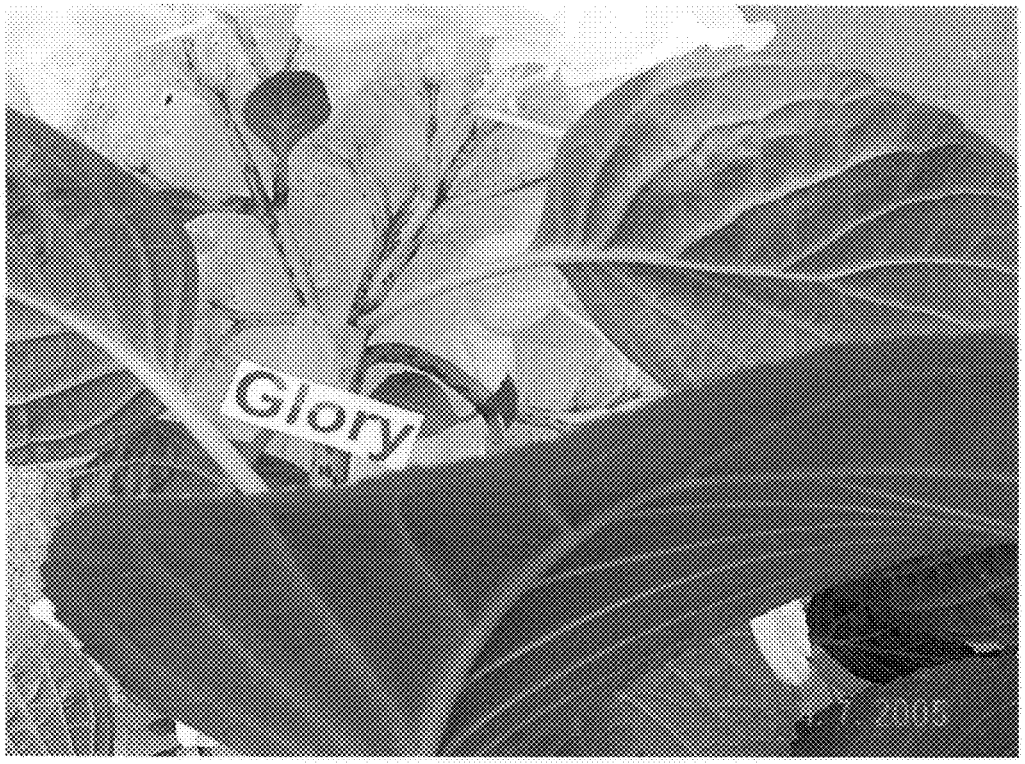
FIG. 5 is a close-up view of a non-woody portion of the stem, showing lenticels on the stem.
Figure 6:
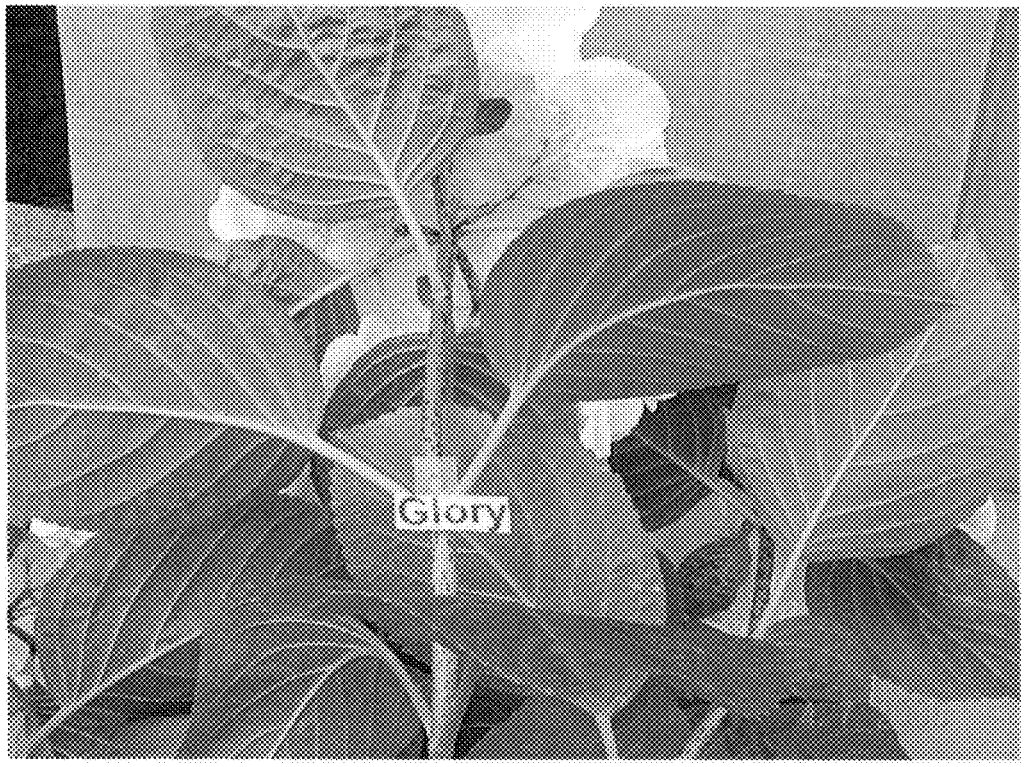
FIG. 6 a view of a non-woody portion of the stem, showing lenticels on the stem
Figure 7:
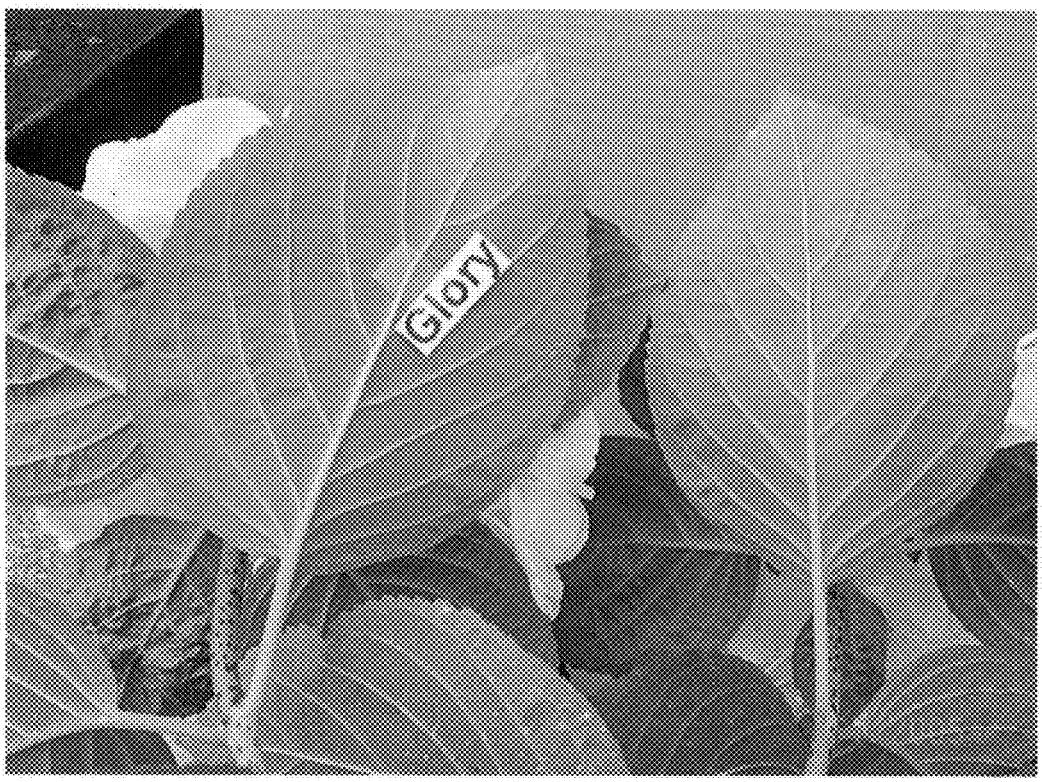
FIG. 7 is a close-up view of the abaxial surface of a mature leaf.
Figure 8:
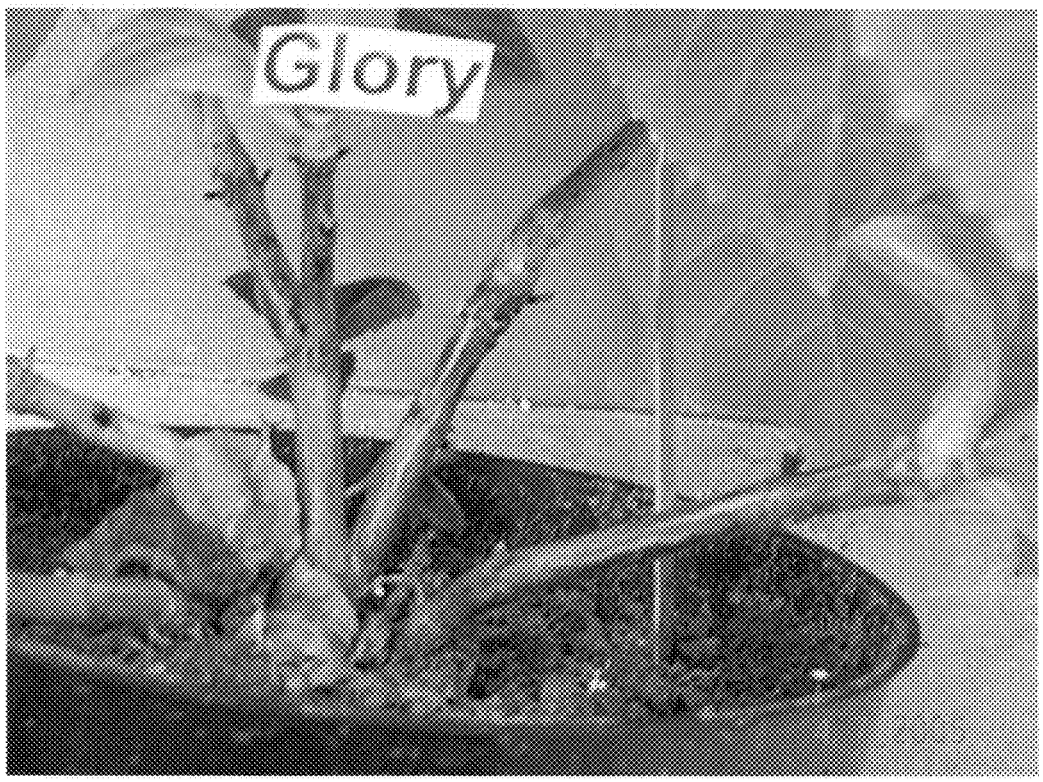
FIG. 8 is a close-up view of the woody portion of the stem.

The plants shown in the figures are approximately 1 years old. The plant started out as cuttings, taken from the stem of a grown plant.

'Glory' has not been observed under all possible environmental conditions. The phenotype may vary significantly with variations in environment such as temperature, light intensity and day length. Color determinations were made with The Royal Horticultural Society (R.H.S.) Colour Chart. The plant:

*Origin.*—Controlled cross between the unpatented seed parent 'Libelle' and the unpatented pollen parent 'Snowball'.

*Form.*—Upright, compact shrub. A typical plant with a mature inflorescence that is ready for sale is approximately 17" high and has a diameter of 16" when grown in a 4" pot with appropriate soil amendments.

*Growth.*—Upright, vigorous growth habit. Inflorescence is large. The plant branches easily with shoots forming at the base of the plant. Lateral branches are similar in appearance and form to the main stems.

*Stems.*—Lenticels are present. Lenticels are RHS 59B red-purple group, and 1 to 4 mm in length. Stems become woody as they age. The color of typical young stems and young lateral branches is RHS 145 A (green group). Stems and lateral branches are approximately 12" tall and 5 to 7 mm in width. Stems and branches are smooth.

*Foliage.*—Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the leaf surface.

*Color.*—Mature leaves have an upper side that is RHS 147 A (yellow-green group), and an under side that is RHS 138 B (green group). Leaves are pinnately veined. Vein color is RHS 145 C (green group).The midvein and veins branching off the midvein are large and prominent on the underside of the leaves. Leaves are as wide as 5.75" and 7.25" long. Petioles are typically 1" to 1.5" long. Petioles are 2 cm long by 4 mm wide. Petioles are RHS 145 C (green group).

Buds:

*Form.*—Globose with 4 to 5 connate petals. The majority of buds have sepals. Buds are approximately 1 mm by 1 mm when very young. Buds can be 5 mm in diameter and still unopened.

*Aspect.*—Smooth.

*Arrangement.*—Borne on branched panicles.

Inflorescence:

*Form.*—Paniculate. Terminal. As many as 50 or more individual flowers (florets) per inflorescence. Both sepalous florets and non-sepalous florets borne on same panicle. Non-sepalous florets are hidden by sepalous florets. Non-sepalous florets dominate. Flowers do not produce a fragrance. The peduncle or panicle for the inflorescence is strong and upright. Pedicels are typically 25 to 30 mm long for the sepalous florets and 4 mm long for the non-sepalous florets. Pedicels are RHS 155D. The peduncle is RHS 144 A (yellow-green group).

*Size of inflorescence.*—Large. Individual inflorescence size is dependent on the number of florets. A typical inflorescence can grow as large as 9" in diameter, and 5.5" high.

*Shape.*—Clusters of numerous small florets; sepalous florets are flat and overlapping one another. Sepals are persistent.

*Appearance.*—Showy.

Florets:

*General.*—Sepalous florets are perfect and complete.

*Corolla.*—Generally there are 5 petals which fall off as flower matures. Petals are typically 6 mm long and 3 mm wide.

*Stamens.*—10 stamens. Pollen is white — R.H.S. 158C (yellow-white group). Plant produces abundant pollen. Filament is approximately 2 mm long. Anther filament is 1 mm long. Anther can be tall as 4mm and is regular and basally attached. Anther is RHS 148A (yellow-green group).

*Stigma.*—Two to three style each, although most florets have two style. Each style has one stigma. Style is typically 2 mm long.

*Ovary.*—Ovary is partially inferior.

*Sepalous florets.*—General. — Veins dominate on the underside of the sepals.

*Number of sepals.*—4 or 5 sepals per floret, usually 4.

*Aspect of sepals.*—Smooth and glaucescent.

*Shape of sepals.*—Reniform with acuminate apex. Edges often wavy when the floret is young.

*Size of sepals.*—As the florets mature, the sepals enlarge and overlap each other more and more, until, often, there is no space between the sepals when the petals of the florets open. Sepals at maturity are typically 2.5 cm long and 2 cm wide. Flowers are typically 4.5 cm in diameter. Sepal color is RHS 155 (white group) on both upper and lower surfaces in soil that would produce pink sepals in *Hydrangeas* with pigment.

*Fruit.*—none.

I claim:

1. A new and distinct *Hydrangea macrophylla* plant named 'Glory' substantially as herein shown and described.

* * * * *